United States Patent [19]
McGuire

[11] Patent Number: 4,726,716
[45] Date of Patent: Feb. 23, 1988

[54] FASTENER FOR CATHETER

[76] Inventor: Thomas V. McGuire, 5834 Jeffrey Dr., Mt. Olive, Ala. 35117

[21] Appl. No.: 887,635

[22] Filed: Jul. 21, 1986

[51] Int. Cl.⁴ ............................................. A61M 25/02
[52] U.S. Cl. .................................... 604/180; 604/174; 128/DIG. 26
[58] Field of Search ............... 604/174, 177, 180, 284, 604/178, 179; 128/DIG. 15, DIG. 26, 133; 24/306; 248/68.1

[56] References Cited

U.S. PATENT DOCUMENTS

| | | | |
|---|---|---|---|
| 3,726,280 | 4/1973 | Lacount | 128/DIG. 26 |
| 3,834,380 | 9/1974 | Boyd | 604/180 |
| 4,057,066 | 11/1977 | Taylor | 604/180 |
| 4,149,539 | 4/1979 | Cianci | 604/180 |
| 4,583,976 | 4/1986 | Ferguson | 604/174 |

Primary Examiner—Stephen C. Pellegrino
Assistant Examiner—Ralph Lewis

[57] ABSTRACT

Disclosed herein is a new fastening device for use to fasten a catheter of the type having a first passage and a second passage extending therefrom to the body of the user thereof. Such catheters are known as Foley catheters and the inventive fastener includes an opening therethrough, through which is inserted the second mentioned passage of the catheter. The fastener further includes means such as an adhesive for fastening the fastener to the patient, for example, on the leg thereof, and further includes fastening means thereon such as hook and pile fasteners to securely attach the fastener to the catheter at the branching area of the first and second passages thereof.

7 Claims, 4 Drawing Figures

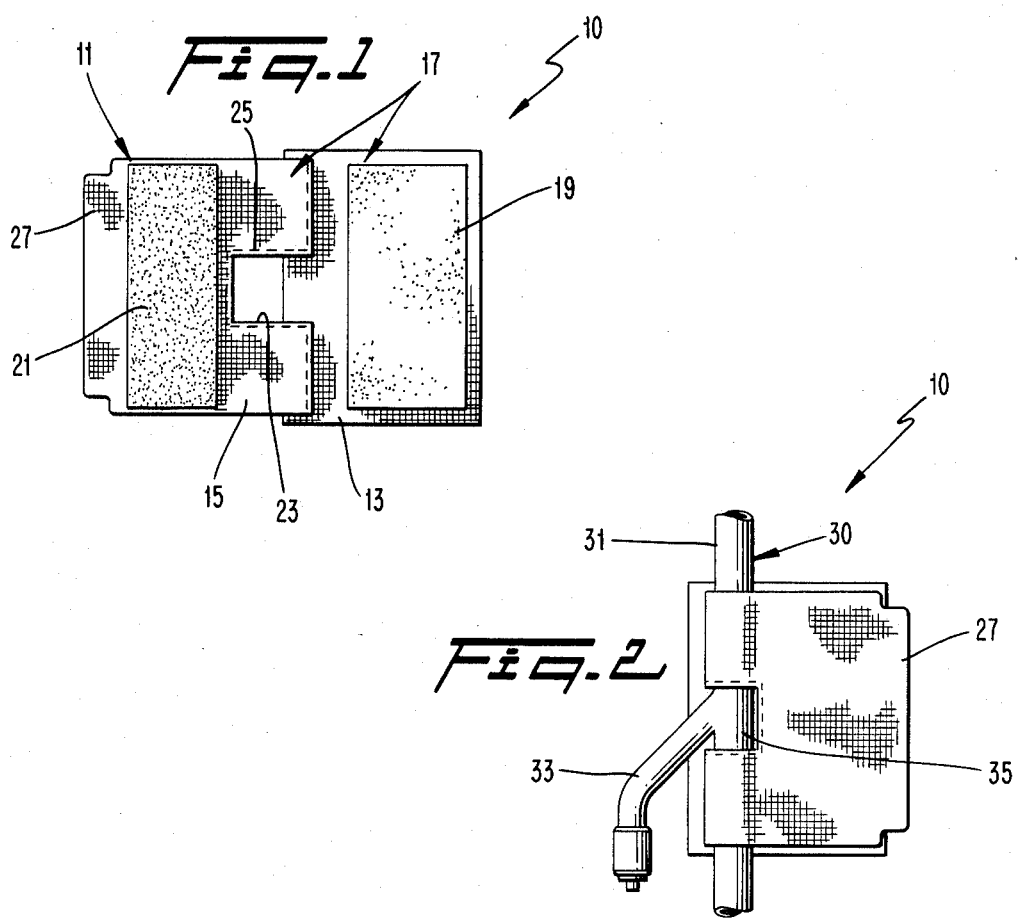

FASTENER FOR CATHETER

BACKGROUND OF THE INVENTION

The Foley catheter is a well-known device for use with patients who have, for some reason, lost control of their bladder. This catheter includes an elongated tube having two passageways therethrough, a first passageway for draining fluid from the bladder and a second passageway which is fluidly connected to a branch tube of the catheter and which is fluidly connected within the bladder to an inflatable balloon. A source of air pressure may be applied to the branch tube so that through the associated passageway in the elongated tube, this balloon may be inflated within the bladder so as to retain the catheter in inserted position therein.

With the catheter structure in mind, a need has developed for an effective device for attaching the catheter to the leg of the patient so that the catheter will not move in situations when the balloon may become deflated. U.S. Pat. Nos. 3,726,280; 3,878,849 and 4,484,913 are known to Applicant, and each discloses a fastening device which may be used with a urinary catheter of the Foley-type. However, these prior art fastening devices are extremely cumbersome and expensive and may cause discomfort to the patient who uses them.

For example, U.S. Pat. No. 3,726,280 to Lacount discloses a fastening device which fastens the catheter to the leg at the area of the branch between the branch tube and the elongated tube thereof. However, the Lacount device requires an elongated strap 34 which extends completely about the leg of the user thereof. Such a strap is extremely uncomfortable and may cause varying degrees of discomfort for different extents of flexure of the thigh muscles of the associated leg. Accordingly, a need has developed for a fastening device for a urinary catheter of the Foley-type which is inexpensive to manufacture, easy to install and which minimizes discomfort to the patient.

SUMMARY OF THE INVENTION

Thus, in order to overcome the deficiencies of the prior art, the present invention has been developed. The present invention includes the following interrelated features:

(a) The inventive fastener includes an elongated flexible body which may be formed of one piece or, alternatively of two pieces fastened together by any desired means such as sewing, adhesive, etc.

(b) This body has, at a central location thereon, an opening therethrough which may be round, square or of other configuration. The opening is sized so that when the fastener is used to fasten a urinary catheter of the Foley-type to the leg of the patient, the branch tube thereof may be inserted through the opening so as to securely define the location of the fastener on the catheter.

(c) On one face of the elongated flexible body, fastening means is attached thereto having complimentary halves which may engage one another when the elongated flexible body is folded on top of itself so as to engage the fastening halves together. The fastening means may be of any desired type such as hook and pile fasteners, snap fasteners and the like.

(d) On the opposite face of the elongated flexible body, approximately one-half of the surface thereof is covered with an adhesive which may be exposed, preferably, by peeling off a backing associated therewith.

(e) Thus, to use the inventive fastener, the branch tube of the catheter may be inserted through the opening in the fastener whereupon the elongated flexible body may be folded upon itself to engage the fastening means halves with one another, whereupon the peel-off backing may be peeled off revealing the adhesive thereunder which may be used to fasten the fastener to the leg of the user thereof.

Accordingly, it is a first object of the present invention to provide an improved fastener for a urinary catheter of the Foley-type.

It is a further object of the present invention to provide such a fastener including means thereon which interact with the catheter so as to prevent movements of the catheter with respect thereto in assembly.

It is a still further object of the present invention to provide such a catheter with an opening through which the branch tube of the catheter may be extended so as to provide such secure attachment.

It is a yet further object of the present invention to provide such a fastener which may be easily attached to the leg of the user thereof and which may be easily and securely fastened to the associated catheter.

These and other objects, features and advantages of the present invention will be better understood from the following detailed description of the preferred embodiments when read in conjunction with the appended drawing figures.

BRIEF DESCRIPTION OF THE DRAWINGS

FIG. 1 shows a top view of the fastener of the present invention in an open condition.

FIG. 2 shows a further top view of the inventive fastener as folded upon itself to secure a catheter thereto.

FIG. 3 shows a side view of the fastener seen in FIG. 1.

FIG. 4 shows a view similar to the view of FIG. 1 but showing an alternative construction of the inventive fastener.

SPECIFIC DESCRIPTION OF THE PREFERRED EMBODIMENTS

With reference, first, to FIGS. 1-3, it is seen that the fastener 10 includes an elongated flexible body 11 which in the figures is seen to include a first piece 13 and a second piece 15. As seen in FIG. 1, a first surface 17 of the fastener encompassing both pieces 13, 15 has attached thereto a hook and pile-type fastener. In FIG. 1, the hook portion 19 thereof is seen to be mounted on the first piece 13 whereas the pile portion 21 is seen to be attached to the second piece 15. It should be stressed, that this configuration may be reversed as desired and it does not matter on which piece the respective hook and pile portions are mounted. The fastening means 19, 21, may be attached to the body 11 by any suitable means such as adhesive, stitching, etc.

Centrally located on the body 11 is an opening 23 which is shown as surrounded by stitching 25 which is used not only to reinforce the opening 23 but which extends further to assemble the pieces 13, 15 together.

With reference to FIG. 2, a urinary catheter 30 is seen to include an elongated tube 31 and a branch tube 33 which branches therefrom at an intersecting area 35. As seen in FIG. 2, the branch tube 33 is inserted through the opening 23 whereupon the elongated body 11 may be folded upon itself so that the pile portion 21 of the fastening means 19, 21 is brought into engagement with the hook portion 19 thereof so as to fasten the elongated body 19 about the catheter 30. For this purpose, the piece 15 includes a tab portion 27 which may be grasped by the user thereof to facilitate the folding over of the piece 15 over the piece 13 to engage the fastening means 19, 21.

With reference now to FIG. 3, it is seen that the piece 13 has on its face opposite to the face on which is located the hook portion 19, an adhesive layer 28 which is covered by a backing paper 29 which may be selectively peeled off to reveal the adhesive 28. Thus, with the fastener 10 in the orientation shown in figure 2 as mounted about the catheter 30, the backing paper 29 may be peeled off the adhesive 28 whereupon the fastener 10 may be adhered to the leg of the user thereof in a desired location.

With reference now to FIG. 4, a further embodiment of the present invention is seen, and like features are designated by like primed reference numerals. The fastener 10' is seen to include an elongated flexible body 14 formed of a single piece. The body 14 includes the tab 27', the hook portion 19', and the pile portion 21' of the fastening means. Approximately centrally located on the body 14 is an opening 24 which is substantially circular in configuration and designed of a size to securely accomodate therethrough the branch passage 33 of the urinary catheter 30 as seen in FIG. 2. Otherwise, the fastener 10' is identical to the fastener 10 including the adhesive 28 with the peel-off backing paper 29 as shown in figure 3.

In the use of the present invention, as explained above, the catheter 30 is attached to the fastener 11 by inserting the branch tube 33 of the catheter 30 through the opening 23 or 24 of the fastener whereupon the elongated flexible body 11 or 14 is folded upon itself to the position shown in FIG. 2 wherein the fastening means 19, 20 fastens the fastener 11 about the catheter 30. Thereupon, the backing paper 29 may be peeled off the fastener to thereby reveal the adhesive 28 which may be used to attach the fastener 10 or 10' to the leg of the patient.

Any desired adhesive 28 may be used, however, it has been found that an adhesive known as "stoma-adhesive" is a good choice for use as the adhesive 28, since this adhesive has been designed to be skin-compatible, to be easy to remove from the skin, to be non-irritating to the skin, to have great retentive powers and to resist perspiration. Of course, any adhesive which possesses many or all of these properties may be equally suitable. The body 11,14 may be made of nylon, one way elastic or the like.

Accordingly, an invention has been described in terms of two embodiments which fulfill each and every one of the objectives as set forth hereinabove and overcome all the deficiencies in the prior art discussed above.

Various change modifications and alterations in the teachings of the present invention may be contemplated by those skilled in the art and such modifications, alterations and changes are considered by Applicant to form a part of the present invention. Accordingly, it is intended that the present invention only be limited by the terms of the following claims.

I claim:

1. A fastener for use in fastening a urinary-type catheter to the leg of the user thereof, said catheter being of the type including an elongated tube and a branch tube connected thereto, said fastener comprising:
    (a) an elongated flexible body having first and second faces;
    (b) an opening extending through said body from said first face to said second face and sized to substantially closely receive therethrough said branch tube, said opening being sized to substantially prevent longitudinal movements of said branch tube;
    (c) said first face having first fastening means thereon for fastening said first face in folded configuration about said elongated tube about a fold region in which said opening is located and with said elongated tube supported solely on said first face in said fold region and with said branch tube extending through said opening, the diameter of said elongated tube only being limited by the longitudinal dimension of said first face in a direction substantially perpendicular to the direction of elongation of said fold region;
    (d) said second face having second fastening means thereon for fastening said fastener to said leg.

2. The invention of claim 1, wherein said opening is substantially square.

3. The invention of claim 1, wherein said opening is substantially circular.

4. The invention of claim 1, wherein said elongated flexible body is formed of two pieces fastened together at a region of said opening.

5. The invention of claim 1, wherein said first fastening means comprises a hook and pile fastener.

6. The invention of claim 5, wherein said second fastening means comprises an adhesive covered with a removable backing paper.

7. The invention of claim 1, wherein said body includes a pull tab which may be grasped to fold said first face into said folded configuration.

* * * * *